(12) United States Patent
Vladiskovic et al.

(10) Patent No.: US 7,989,618 B2
(45) Date of Patent: Aug. 2, 2011

(54) LINEZOLID CRYSTALLINE HYDRATE FORM AND LINEZOLID SALTS

(75) Inventors: Chiara Vladiskovic, Milan (IT); Emanuele Attolino, Palaglano (IT); Pietro Allegrini, San Donato Milanese (IT); Gabriele Razzetti, Sesto San Giovanni (IT)

(73) Assignee: DiPharma Francis s.r.l., Baranzate (IT)

( * ) Notice: Subject to any disclaimer, the term of this patent is extended or adjusted under 35 U.S.C. 154(b) by 402 days.

(21) Appl. No.: 12/203,568

(22) Filed: Sep. 3, 2008

(65) Prior Publication Data
US 2009/0062534 A1   Mar. 5, 2009

(30) Foreign Application Priority Data

Sep. 4, 2007 (IT) .............................. MI2007A1718
Jul. 7, 2008 (IT) .............................. MI2008A1233

(51) Int. Cl.
*C07D 413/10* (2006.01)
(52) U.S. Cl. ...................................................... 544/137
(58) Field of Classification Search .................. None
See application file for complete search history.

(56) References Cited

U.S. PATENT DOCUMENTS

| 5,837,870 | A | 11/1998 | Pearlman et al. |
| 6,107,519 | A | 8/2000 | Pearlman |
| 6,444,813 | B2 | 9/2002 | Bergren |
| 6,492,555 | B2 | 12/2002 | Pearlman |
| 6,559,305 | B1 | 5/2003 | Bergren |
| 6,716,980 | B2 | 4/2004 | Pearlman |
| 6,740,754 | B2 | 5/2004 | Pearlman |
| 6,833,453 | B2 | 12/2004 | Perrault et al. |
| 6,887,995 | B2 | 5/2005 | Perrault et al. |
| 7,649,096 | B2 * | 1/2010 | Kumar et al. ................. 548/137 |
| 2006/0111350 | A1 | 5/2006 | Aronhime et al. |
| 2006/0142283 | A1 | 6/2006 | Aronhime et al. |
| 2009/0156806 | A1 | 6/2009 | Colombo et al. |

FOREIGN PATENT DOCUMENTS

| WO | 95/07271 | 3/1995 |
| WO | 2005/035530 A1 | 4/2005 |
| WO | 2007/026369 A1 | 3/2007 |

OTHER PUBLICATIONS

Brickner, Steven J., et al. "Synthesis and Antibacterial Activity of U-100592 and U-100766, Two Oxazolindinone Antibacterial Agents for the Potential Treatment of Multidrug-Resistant Gram-Positive Bacterial Infections," J. Med. Chem, 1996, 39, pp. 673-679.
S.E. Schaus et al., "Dynamic Kinetic Resolution of Epichlorohydrin via Enantioselective Catalytic Ring Opening with TMSN3. Practical Synthesis of Aryl Oxazolidinone Antibacterial Agents," Tetrahedron Letters, vol. 37, No. 44, pp. 7937-7940, 1996.

* cited by examiner

*Primary Examiner* — Rebecca Anderson
*Assistant Examiner* — Alicia L Otton
(74) *Attorney, Agent, or Firm* — Griffin & Szipl, P.C.

(57) ABSTRACT

Linezolid salts, useful as such and as intermediates in a process for the preparation of novel and known crystalline linezolid forms, in particular known as Form III.

8 Claims, 5 Drawing Sheets

LINEZOLID CRYSTALLINE HYDRATE FORM AND LINEZOLID SALTS

This application claims priority from Italian Patent Application No. MI2007A1718, filed Sep. 4, 2007, and from Italian Patent Application No. MI2008A1233, filed Jul. 7, 2008, the entire disclosures of which are incorporated herein by reference.

FIELD OF THE INVENTION

The present invention relates to a novel linezolid crystalline hemihydrate form and to addition salts of linezolid useful in its preparation.

TECHNOLOGICAL BACKGROUND

Linezolid, i.e. [(S)—N-[[3-(3-fluoro-4-morpholinyl)phenyl]-2-oxo-5-oxazolidinyl]methyl]acetamide], having the following formula

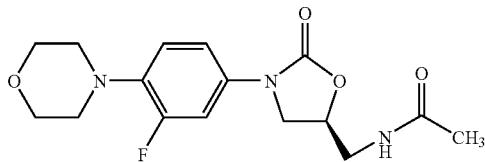

is an antibacterial agent, whose preparation is disclosed in WO 95/07271. Various polymorphic forms of linezolid are known, for example, U.S. Pat. No. 6,559,305 claims a linezolid crystalline form referred to as Form II. According to this document, another crystalline form is known from J. Med. Chem., 39(3), 673-679 (1996), also referred to as Form I.

US 2006/0142283 claims a crystalline Form IV, also claimed by WO 2005/035530 but as crystalline Form III, which is stated to be more compact and less electrostatic than the Form II. US 2006/0111350 discloses various polymorphic forms and claims linezolid in the hydrate form. Finally, WO 2007/026369 discloses the amorphous form of linezolid.

It is well known that the physical properties of a drug are fundamental for the preparation of pharmaceutical forms in pharmaceutical technique. In particular, solid drugs characterized by not very dense, highly electrostatic crystals are difficult to mill. A further important characteristic is the flowability of the powders resulting from the milling of the solid: in fact, when the powdered compound particles do not flow, they stick to one another. A further important aspect, which is affected by the crystalline structure of the product, is its dissolution rate in aqueous fluids, hence its bioavailability.

There is therefore the need for a novel linezolid crystalline form and linezolid salts, having more advantageous characteristics for use in the pharmaceutical technique and in clinics.

SUMMARY OF THE INVENTION

It has been found that linezolid can exist in a novel crystalline hemihydrate form. A further object of the invention are linezolid addition salts, useful as such or for the preparation of the novel crystalline form of the invention and of other known forms, in particular of the Forms II and III.

BRIEF DESCRIPTION OF THE ANALYTICAL METHODS

The novel crystalline hemihydrate form, as well as linezolid dihydrochloride and sulfate salts, were characterized by potentiometric and argentimetric titration, X-ray powder diffraction (XRPD), 1H-NMR nuclear magnetic resonance spectrometry and differential scanning calorimetry (DSC). The water content in the compounds was determined by titration according to Karl-Fischer.

The X-ray diffraction spectrum (XRPD) was recorded with an automatic diffractometer θ/θ for powders and liquids manufactured by Ital-Structures, under the following operative conditions: radiation CuKα (λ=1.5418 Å), scansion with angular interval 3-40° in 2θ with angular step of 0.03° for 1 sec.

1H-NMR spectra were recorded on a spectrometer Varian Mercury 300, using DMSO-d6 as the solvent. DSC thermograms were recorded with the differential scansion calorimeter Mettler-Toledo DSC 822e, under the following operative conditions: aluminium capsules, 30-300° C. interval at the rate of 10° C./min, with nitrogen as purging gas (80 ml/min).

Particle size was determined with the known laser light scattering technique using a Malvern Mastersizer MS1 instrumentation under the following operative conditions:
  300RF mm lens, with 2.4 mm laser beam length;
  500 mg sample dispersed in 10 ml hexane (ACS reagent) with 1% SPAN 85®, no presonication, 2500 rpm stirring rate.

DETAILED DISCLOSURE OF THE INVENTION

Figure 1:
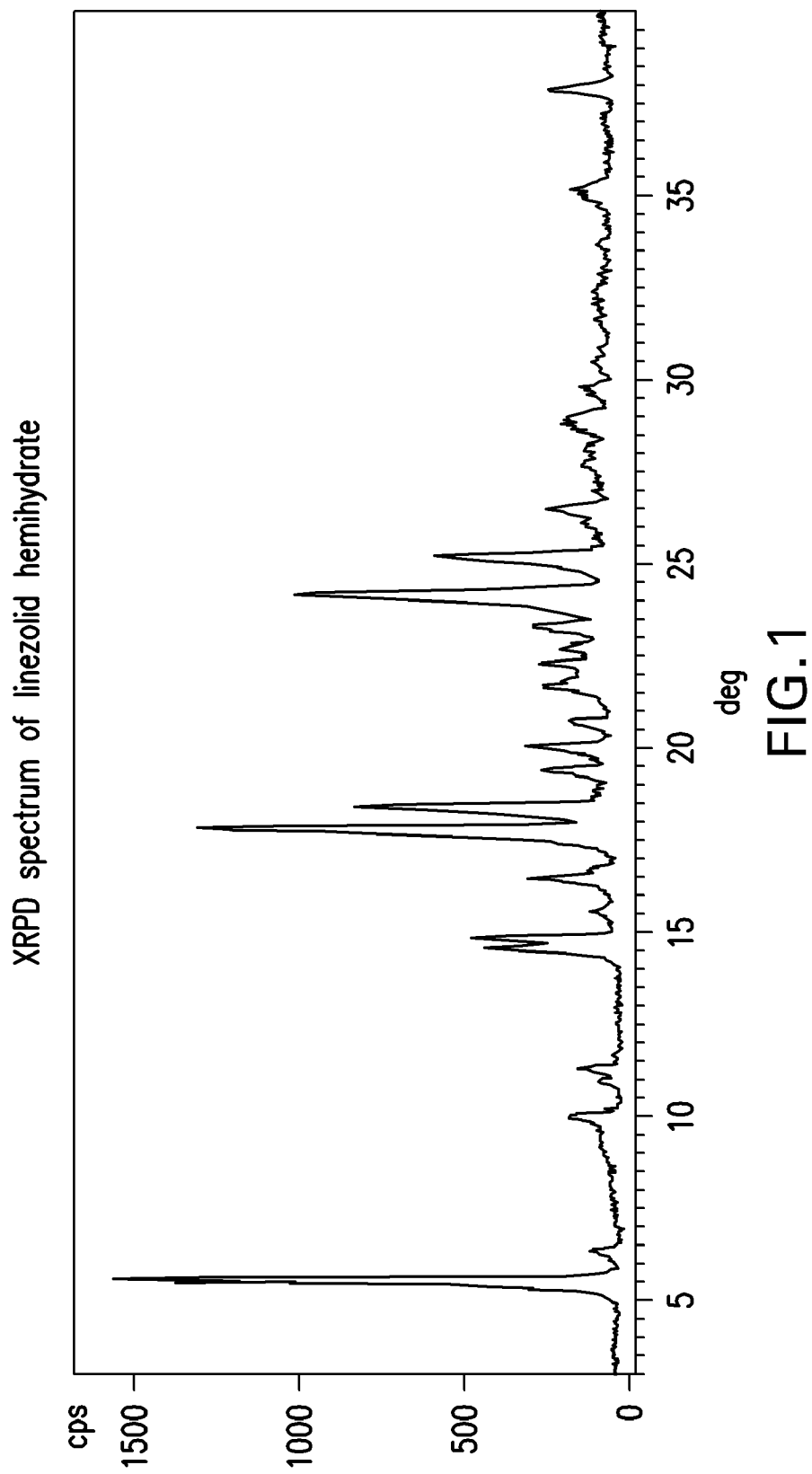
FIG. 1: XRPD spectrum of linezolid hemihydrate.
Figure 2:
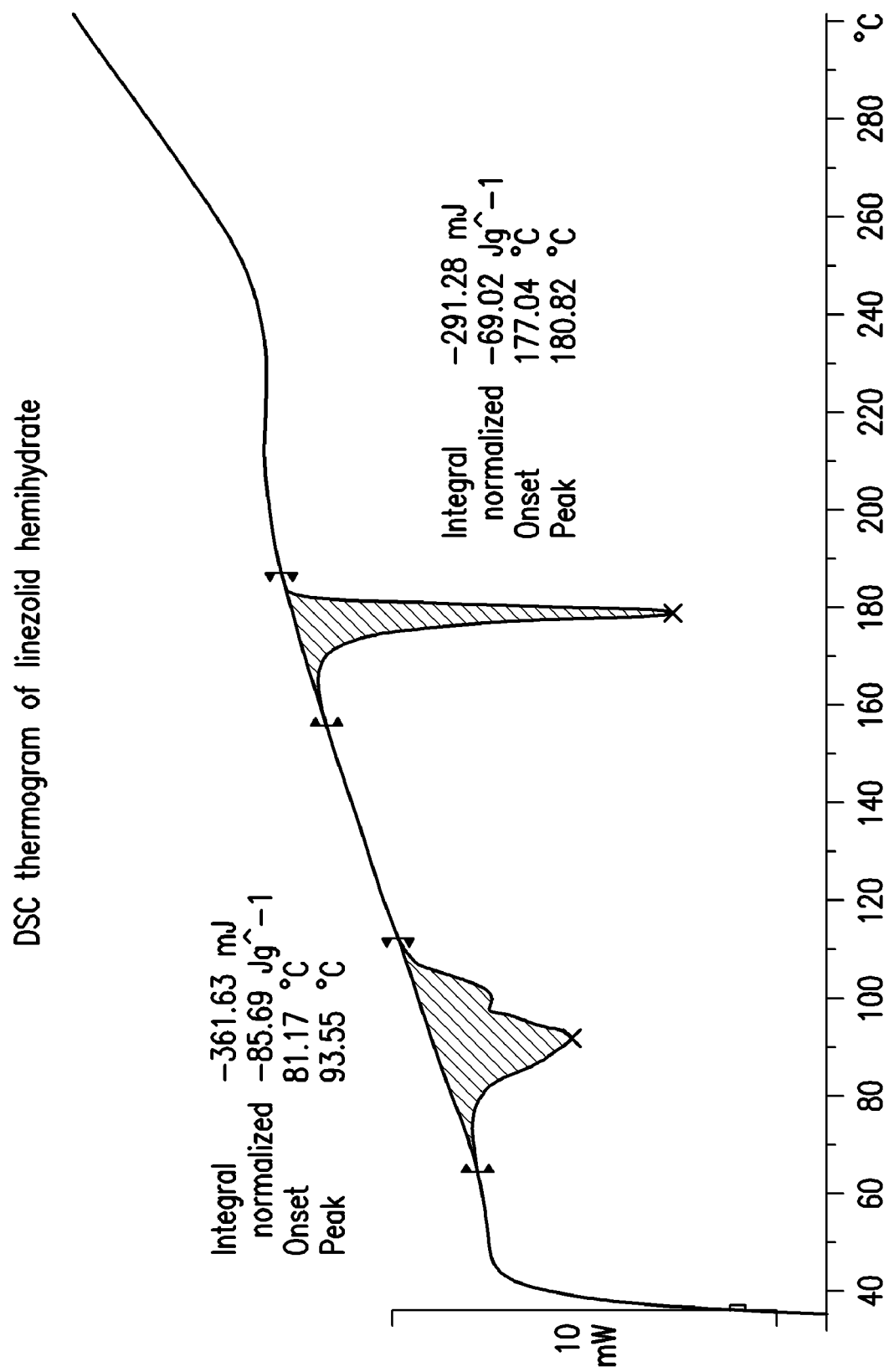
FIG. 2: DSC thermogram of linezolid hemihydrate.

An object of the present invention is linezolid in the approximately hemihydrate crystalline form, with water content approximately ranging from 2.5 to 3.5% w/w; preferably approximately from 2.6 to 2.8% w/w. This form is characterized by a DSC thermogram substantially as reported in FIG. 2, with two exothermic peaks at 94 and 181±2° C.; and an XRPD spectrum substantially as illustrated in FIG. 1, wherein the most intense diffraction peaks fall at 5.4; 14.5; 14.8; 16.3; 17.6; 18.3; 19.2; 19.9; 23.2; 24.0 and 25.1±0.2° in 2θ.

The linezolid approximately hemihydrate crystalline form can be prepared by a process comprising:
  providing a water solution of a linezolid addition salt;
  cooling of the solution at a temperature below 10° C.;
  treatment of the solution with a strong basic agent; and
  recovery of the resulting solid.

Linezolid, used as the starting material, can be in either one of its known crystalline forms or in the amorphous form, which can be easily dissolved in water, or as a solution of a linezolid crude preparation.

A linezolid addition salt can be, for example, a pharmaceutically acceptable acid addition salt thereof, e.g. with a strong acid, typically linezolid dihydrochloride, linezolid sulphate or linezolid camphorsulfonate; preferably linezolid dihydrochloride.

A linezolid addition salt can be obtained e.g. by treating a solution of linezolid in an organic aprotic solvent, for example acetone, tetrahydrofuran, ethyl acetate or acetonitrile, preferably acetone or tetrahydrofuran, with a concentrated aqueous solution of a strong acid, optionally re-crystallizing the precipitate, and recovering the product e.g. by filtration or centrifugation, if desired, followed by drying under vacuum. Preferred examples of strong acids are hydrochloric acid, sulfuric acid and camphorsulfonic acid.

Figure 3:
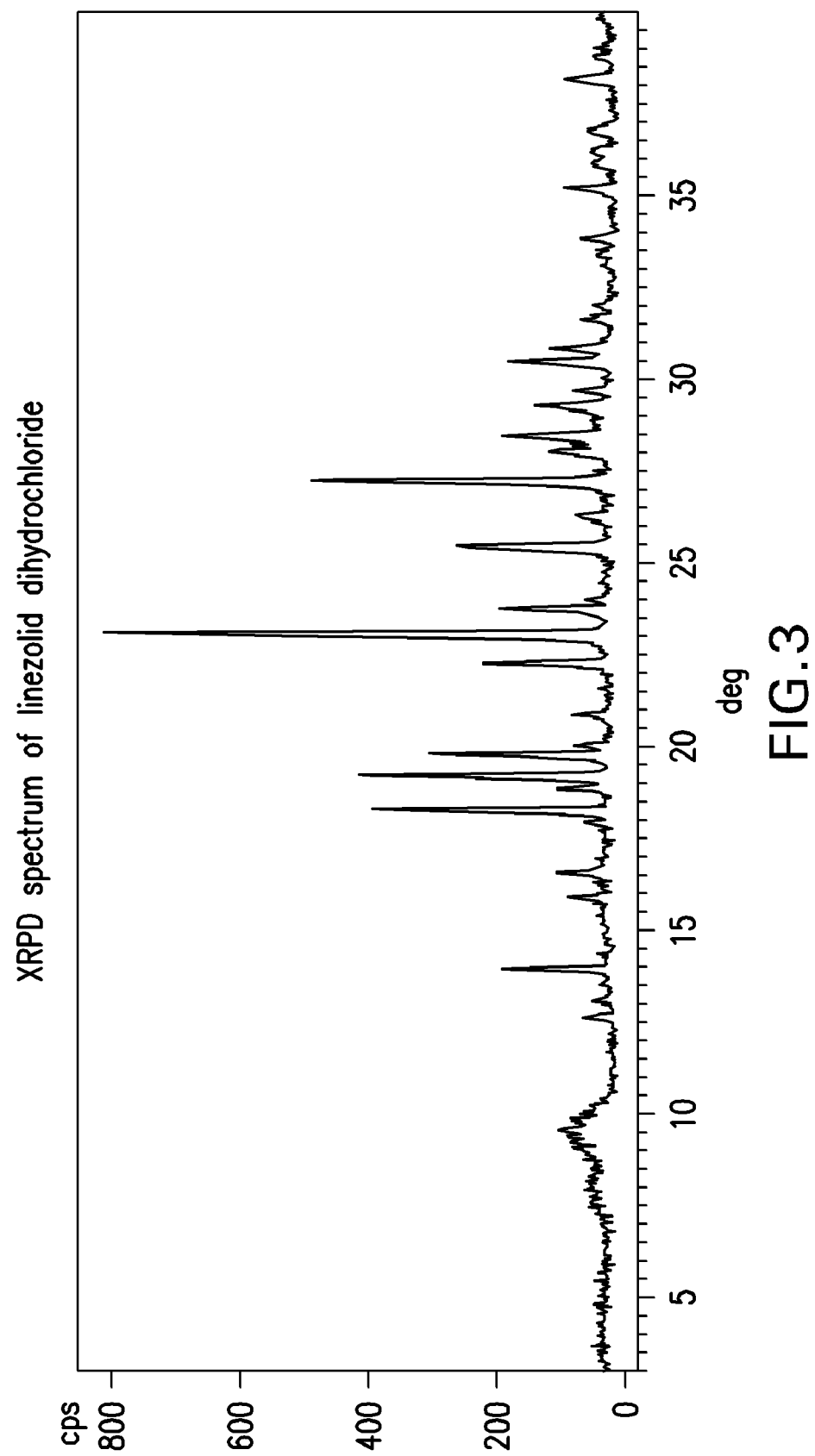
FIG. 3: XRPD spectrum of linezolid dihydrochloride.
Figure 4:
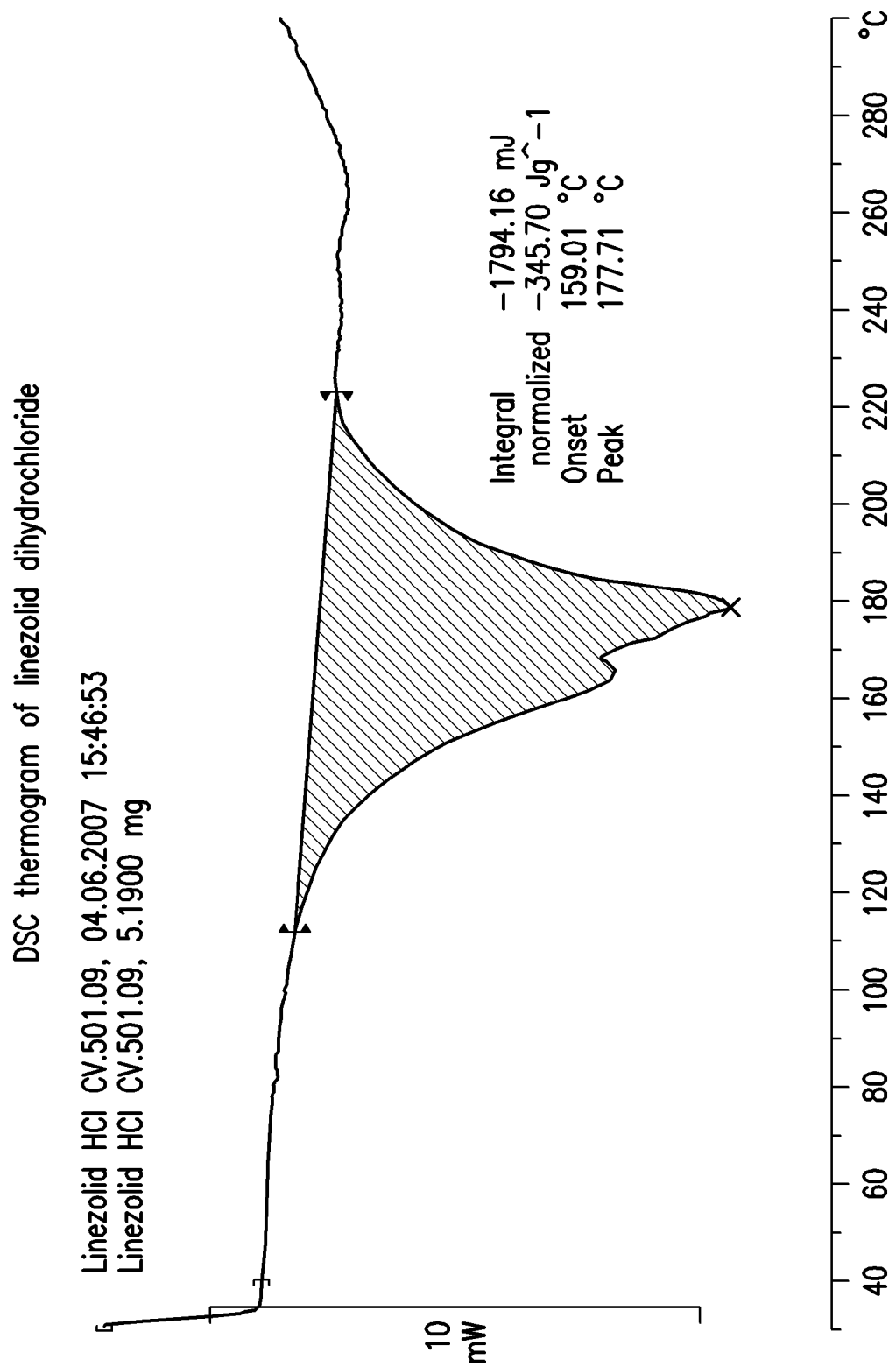
FIG. 4: DSC thermogram of linezolid dihydrochloride.

The resulting linezolid hydrochloride is a water-soluble crystalline solid, characterized by a DSC thermogram substantially as reported in FIG. 4, with an exothermic peak at 178±2° C.; and an XRPD spectrum substantially as illustrated in FIG. 3, wherein the most intense diffraction peaks fall at 13.9; 18.2; 19.1; 19.7; 22.2; 22.9; 23.6; 25.3; 27.1; 28.4±0.2° in 2θ.

According to the potentiometric and argentimetric titrations, the resulting linezolid hydrochloride is a dihydrochloride, i.e. a linezolid addition salt with two equivalents of hydrochloric acid. The chloride titre is indeed 17.71% (theor. dihydrochloride 17.77%), while the theoretical titre for the monohydrochloride is 9.75%. Analogously, potentiometric titration with sodium hydroxide evidences two equivalence points and double sodium hydroxide consumption compared with the theoretical monohydrochloride salt, thus conforming this is the dihydrochloride salt.

Figure 5:
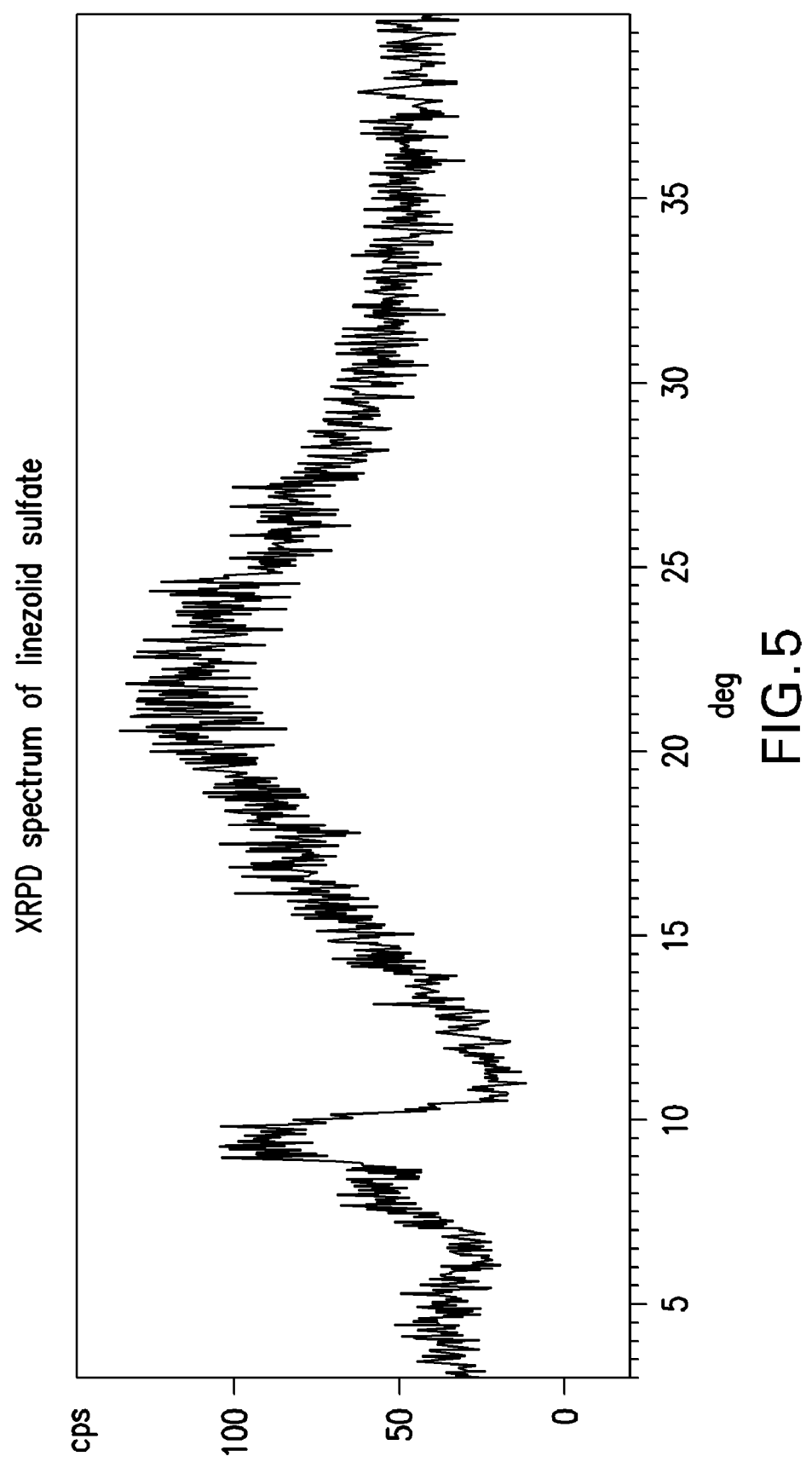
FIG. 5: XRPD spectrum of linezolid sulfate.

The resulting Linezolid sulfate is an amorphous, hygroscopic, water-soluble solid, characterized by an XRPD spectrum substantially as reported in FIG. 5.

The linezolid dihydrochloride, sulfate and camphorsulfonate salts, in particular in the forms herein reported, are novel and are a further object of the invention.

The linezolid addition salt is then dissolved in water and the concentration of the linezolid in the starting water solution can approximately range from 2 to 35% w/w, preferably approximately from 15 to 20% w/w.

The solution can be cooled to a temperature below 10° C., preferably below 5° C., in particular around 0-3° C., in order to promote, upon addition of the basic agent, the precipitation of linezolid in the crystalline hemihydrate form. If desired, crystallization can be promoted by seeding with crystals of linezolid in crystalline hemihydrate form previously obtained.

A strong basic agent can be, for example, a strong inorganic base, e.g. an alkali or alkaline-earth metal hydroxide, preferably sodium, potassium or barium hydroxide; or a strong organic base, such as a sodium or potassium $C_1$-$C_4$ alkoxide, preferably sodium or potassium ethoxide, butoxide or tert-butoxide; more preferably sodium or potassium hydroxide.

The solid product can be recovered according to known techniques, for example by filtration or centrifugation, optionally followed by drying under vacuum. The product is preferably isolated by filtration, followed by drying under vacuum at a temperature approximately ranging from 35 to 40° C.

The resulting linezolid crystalline hemihydrate form, and linezolid dihydrochloride, sulfate and camphorsulfonate salts, in particular in the forms reported above, have purity degree equal to or higher than 99.5%, in particular equal to or higher than 99.9%, as determined by HPLC, which is suitable to fulfil the regulatory requirements for pharmaceuticals.

The size of the resulting crystals of linezolid hemihydrate and dihydrochloride and camphorsulfonate salts is characterized by a $D_{50}$ value approximately ranging between 25 and 250 µm, wherein $D_{50}$ is the particle diameter in which 50% (by volume) of the particles sample have diameter of or below the specific value. This specific value, if desired, can be reduced by micronization or fine grinding.

The novel linezolid hemihydrate form and the linezolid dihydrochloride, sulfate and camphorsulfonate salts can be used in therapy and veterinary medicine for the treatment of the same diseases as those treated with linezolid.

Linezolid in the crystalline hemihydrate form of the invention, contrary to the known crystalline Form II, is not electrostatic and is therefore well suited for the preparation of compositions for the pharmaceutical use.

A further object of the invention is a pharmaceutical composition comprising, as the active ingredient, the novel linezolid crystalline hemihydrate form or the dihydrochloride, sulfate or camphorsulfonate linezolid salts, in particular in the forms herein reported, or mixtures thereof, and one or more pharmaceutically acceptable excipients, for example one or more diluents and/or carriers selected from those conventionally used in the art.

The pharmaceutical composition can further contain as the active ingredient at least one, preferably one, two or three, of the known linezolid forms.

Those skilled in the art will be able to choose the amount of the individual forms of linezolid and/or dihydrochloride, sulfate and/or camphorsulfonate salts, for the preparation of the formulation. The dosage is left to the discretion of the physician.

The linezolid dihydrochloride, sulfate and camphorsulfonate salts, in particular in the forms reported above, being highly water-soluble at low temperature, are particularly useful as intermediates in the process described above for the preparation of linezolid in the novel crystalline hemihydrate form and of known linezolid forms, in particular linezolid Form II and Form III, as designated in U.S. Pat. No. 6,559,305 and WO 2005/035530, respectively. A further object of the invention is a process for the purification of linezolid, comprising the conversion of linezolid to the novel approximately hemihydrate crystalline form, by the process herein described for its preparation, and its subsequent conversion to a known linezolid form. By way of example, the approximately hemihydrate crystalline form of the invention can be converted to the known crystalline Form III, by a process comprising heating the neat solid at approximately 90° C. for about 1 h; or it can be converted to the known Form II, for example by a process comprising the formation of a suspension thereof in water at a temperature approximately ranging from 0° C. to room temperature, and the recovery of the crystalline solid, e.g. by filtration.

The processes for the purification of linezolid, comprising the formation of linezolid in the approximately hemihydrate crystalline form and its the conversion to the known linezolid Forms II or III, are a further object of the invention.

The thus purified Linezolid, for example the Form II or III, has purity equal to or higher than 99.5%; preferably equal to or higher than 99.9%, as determined by HPLC.

A further object of the invention is a process for the preparation of linezolid in the crystalline Form III, as defined in WO 2005/035530, comprising:
  obtaining an aqueous solution of a linezolid addition salt;
  treatment of the solution with an alkali metal carbonate, in the presence of a low-boiling organic solvent;
  separation of the phases;
  treatment of the organic solution with toluene;
  removal of the low-boiling organic solvent;
  crystallization from toluene and recovery of the product.

A linezolid addition salt can be obtained as described above. Preferred examples of the salts are the dihydrochloride, sulfate and camphorsulfonate, in particular the dihydrochloride, preferably in the forms herein described.

An aqueous solution of a linezolid addition salt can be obtained e.g. by suspending the salt in water or preferably in a mixture of water with a solvent selected for example from ethyl acetate, acetonitrile, tetrahydrofuran, methanol and ethanol, preferably ethyl acetate; and heating the mixture at a temperature approximately ranging from 45 to 75° C.

The concentration of the aqueous solution of the salt can approximately range from 5% to 80% w/w; preferably around 50% w/w.

An alkali metal carbonate can be for example sodium or potassium carbonate salt, preferably potassium carbonate.

A low-boiling solvent can be a polar or apolar, protic or aprotic, organic solvent, that has a boiling point below 80-85° C. and is able to solubilize linezolid. Preferred examples are methylene chloride, chloroform, acetone, tetrahydrofuran, methanol, ethanol, ethyl acetate and acetonitrile; in particular ethyl acetate.

The removal of the low-boiling organic solvent is preferably effected by distillation.

The crystallization can be carried out at a temperature approximately ranging from 90° C. to 110° C.

The solid product in the Form III can be isolated according to known techniques, for example by filtration or centrifugation, in particular by filtration, preferably followed by drying under vacuum, at a temperature approximately ranging between 35 and 50° C.

The resulting linezolid crystalline Form III has purity degree equal to or higher than 99.5, in particular equal to or higher than 99.9%, as determined by HPLC; and a particle size with a $D_{50}$ value approximately ranging between 25 and 250 μm.

The following examples illustrate the invention.

Example 1

Linezolid Dihydrochloride 20 g of linezolid are dissolved in 750 ml of acetone at about 30° C. The solution is kept at about 30° C. and 8 ml of concentrated hydrochloric acid (37% w/w aqueous solution) are added, thus immediately causing linezolid dihydrochloride to precipitate as a white solid. The mixture is kept under stirring at about 30° C. for approximately 30 minutes, then refluxed under stirring for about 2 hours. The mixture is left to cool to room temperature, then cooled on ice-water bath, under stirring, for about 2 hours. A white solid precipitates which is filtered with suction, washed with 30 ml of acetone and dried under vacuum at about 50° C.

A solid water-soluble crystalline product is obtained, characterized by an XRPD spectrum substantially as reported in FIG. 3, wherein the most intense diffraction peaks fall at 13.9; 18.2; 19.1; 19.7; 22.2; 22.9; 23.6; 25.3; 27.1; 28.4±0.2° in 2θ; and by a DSC thermogram substantially as reported in FIG. 4, characterized by an exothermic peak around 178±2° C. The acid-base potentiometric titre is double while the argentimetric one is 17.71% (theor. dihydrochloride 17.77%). Purity 99.8% as determined by HPLC.

$^1$H NMR (300 MHz, DMSO-d6), ppm: 8.37 (bt, 1H), 7.50 (dd, 1H, J=15.3 Hz, J=2.7 Hz), 7.10 (m, 2H), 4.68 (m, 1H), 4.05 (t, 1H, J=9.0 Hz), 3.70 (m, 5H), 3.36 (t, 2H, J=5.1 Hz), 3.07 (t, 4H, J=4.5 Hz), 1.80 (s, 3H).

Example 2

Linezolid Dihydrochloride 20 g of linezolid are dissolved in 750 ml of tetrahydrofuran at about 30° C. The solution is treated as described in Example 1, to obtain a linezolid dihydrochloride precipitate as a white solid, which is filtered with suction, washed with 30 ml of tetrahydrofuran and dried under vacuum at about 50° C.

Linezolid dihydrochloride is obtained in a crystalline form, having the same characteristics as reported for the product obtained in Example 1.

Example 3

Linezolid Sulfate 5 g of linezolid are dissolved at about 40° C. in 150 ml of THF. The solution is kept at about 40° C. and 0.85 ml of concentrated sulfuric acid (98% w/w $H_2SO_4$) are added, thus immediately causing linezolid sulfate to precipitate as a white solid. The mixture is refluxed, under stirring, for about 30 minutes, then left to cool first to room temperature then on an ice-water bath, stirring for about 30 minutes. A white solid precipitates, which is filtered with suction, washed with 5 ml of THF and dried under vacuum at about 50° C.

An amorphous, water-soluble solid product is obtained, characterized by an XRPD spectrum substantially as reported in FIG. 5.

$^1$H NMR (300 MHz, DMSO-d6), ppm: 8.21 (bt, 1H), 7.47 (dd, 1H, J=15.3 Hz, J=2.7 Hz), 7.10 (m, 2H), 4.68 (m, 1H), 4.05 (t, 1H, J=9.0 Hz), 3.70 (m, 5H), 3.45 (m, 2H), 2.97 (t, 4H, J=4.5 Hz), 1.81 (s, 3H).

Purity 99.7% as determined by HPLC.

Following an analogous procedure, by reaction with camphorsulfonic acid, linezolid camphorsulfonate is obtained.

Example 4

Linezolid Hemihydrate Starting from Linezolid dihydrochloride 4 g of linezolid dihydrochloride are dissolved at room temperature in 20 ml of water. The solution is cooled to a temperature of about 0-2° C., and 2.5 g of a NaOH 50% w/w aqueous solution are added, thus immediately causing linezolid hemihydrate to precipitate. A white solid is obtained which is filtered with suction, thoroughly washed with water and dried under vacuum at about 35-40° C. The obtained crystalline solid is characterized by an XRPD spectrum substantially as reported in FIG. 1, wherein the most intense diffraction peaks fall at 5.4; 14.5; 14.8; 16.3; 17.6; 18.3; 19.2; 19.9; 23.2; 24.0 and 25.1±0.2° in 2θ and a DSC thermogram substantially as reported in FIG. 2, characterized by two exothermic peaks at 94 and 181±2° C. Purity 99.8% as determined by HPLC.

$^1$H NMR (300 MHz, DMSO-d6), ppm: 8.20 (bt, 1H), 7.45 (dd, 1H, J=15.0 Hz, J=2.7 Hz), 7.10 (dd, 1H, $J_1$=9.0 Hz, $J_2$=2.4 Hz), 7.00 (t, 1H, J=9, 3 Hz), 4.68 (m, 1H), 4.05 (t, 1H, J=9.0 Hz), 3.70 (m, 5H), 3.40 (m, 2H), 2.93 (t, 4H, J=4.6 Hz), 1.81 (s, 3H).

Example 5

Linezolid Form III Starting from Linezolid Dihydrochloride

Linezolid dihydrochloride (40 g, 97.5 moles) is suspended in water (40 ml) and ethyl acetate (480 ml). The mixture is heated to a temperature ranging from 60-65° C. to complete dissolution of the solids, then a potassium carbonate solution (20 g) in water (40 ml) is slowly dropwise added. The reaction mixture is kept under stirring to obtain two clear phases which are separated while hot. The organic phase is washed with water then diluted with toluene. Ethyl acetate is distilled off and the mixture is heated to a temperature around 100° C., until Linezolid Form III starts crystallizing. The distillation is stopped and the mixture is left to slowly cool down to room temperature. The solid is filtered and then dried to obtain 30.0 g of crystalline linezolid, in 92% yield. The resulting crystalline product is characterized by the same XRPD spectrum as that reported for the crystalline Form III, described in WO 2005/035530; and a purity of 99.9% as determined by HPLC.

The invention claimed is:

1. A process for the preparation of linezolid in crystalline Form III, comprising the steps of:
    (a) obtaining an aqueous first solution of a linezolid addition salt;
    (b) treating the first solution with an alkali metal carbonate, in the presence of a low-boiling organic solvent, having a boiling point below 85° C.;
    (c) separating phases of the first solution after treatment with the alkali metal carbonate, to provide an organic second solution;
    (d) treating the organic second solution, separated from the first solution, with toluene;
    (e) removing low-boiling organic solvent from the second solution; and
    (f) crystallizing a product from toluene and recovering the product, wherein the product is linezolid in crystalline Form III.

2. A process according to claim 1, wherein the addition salt is chosen from the group consisting of linezolid dihydrochloride, linezolid sulfate and linezolid camphorsulfonate.

3. A process, according to claim 1, wherein the addition salt is linezolid dihydrochloride.

4. A process according to claim 1, wherein the concentration of the aqueous first solution of the linezolid addition salt approximately ranges from 5% to 80% w/w.

5. A process according to claim 4, wherein the linezolid addition salt is an acid.

6. A process according to claim 1, wherein the low-boiling organic solvent is a polar or apolar, protic or aprotic, organic solvent.

7. A process, according to claim 6, wherein the low-boiling organic solvent is chosen from the group consisting of methylene chloride, chloroform, acetone, tetrahydrofuran, methanol, ethanol, ethyl acetate and acetonitrile.

8. A process according to claim 1, wherein crystallization is carried out at a temperature approximately ranging from 90° C. to 110° C.

* * * * *